(12) United States Patent
Miles et al.

(10) Patent No.: US 6,508,917 B1
(45) Date of Patent: Jan. 21, 2003

(54) METHOD AND APPARATUS FOR PURIFYING LOW GRADE ACETONITRILE AND OTHER CONSTITUENTS FROM HAZARDOUS WASTE

(75) Inventors: Heather K. Miles, Newark, CA (US); Donald H. Westermann, Greenfield, WI (US); Glenn F. Cunningham, Houston, TX (US)

(73) Assignee: ChemCycles, Inc., Houston, TX (US)

( * ) Notice: Subject to any disclaimer, the term of this patent is extended or adjusted under 35 U.S.C. 154(b) by 0 days.

(21) Appl. No.: 10/155,711

(22) Filed: May 24, 2002

Related U.S. Application Data

(63) Continuation of application No. 09/419,710, filed on Oct. 14, 1999, now Pat. No. 6,395,142.

(51) Int. Cl.[7] .......................... B01D 3/00; C07L 225/00
(52) U.S. Cl. ............................ 203/74; 203/81; 558/435
(58) Field of Search ...................... 203/74, 81; 558/435

(56) References Cited

U.S. PATENT DOCUMENTS

| | | |
|---|---|---|
| 2,107,904 A | 2/1938 | Pool |
| 2,351,157 A | 6/1944 | Semon |
| 2,560,931 A | 7/1951 | Chapman et al. |
| 2,807,573 A | 9/1957 | Robertson |
| 3,201,451 A | 8/1965 | Idol et al. |
| 3,322,814 A | 5/1967 | Iappelli |
| 3,328,458 A | 6/1967 | Iappelli |
| 4,141,826 A | 2/1979 | Alford et al. |
| 4,328,075 A | 5/1982 | Fitzgibbons et al. |
| 4,349,416 A | 9/1982 | Brandt et al. |
| 4,362,603 A | 12/1982 | Presson et al. |
| 4,430,162 A | 2/1984 | Higuchi et al. |
| 4,474,709 A | 10/1984 | Jordan |
| 4,575,434 A | 3/1986 | Frank et al. |
| 5,074,967 A | 12/1991 | Fowlkes |
| 5,094,773 A | 3/1992 | Manzer et al. |
| 5,120,881 A | 6/1992 | Rosenfeld et al. |
| 5,156,748 A | 10/1992 | Meunier et al. |
| 5,292,919 A | 3/1994 | Himes et al. |
| 5,346,595 A | 9/1994 | Clemmer et al. |
| 5,426,208 A | 6/1995 | Himes et al. |
| 6,132,985 A * | 10/2000 | Pierce .................. 435/29 |
| 6,395,142 B1 * | 5/2002 | Miles et al. ............. 203/74 |

FOREIGN PATENT DOCUMENTS

| | | |
|---|---|---|
| EP | 0 890 572 A1 | 7/1997 |
| EP | 0 937 707 A2 | 2/1999 |

* cited by examiner

Primary Examiner—Deborah C. Lambkin
(74) Attorney, Agent, or Firm—Blakely, Sokoloff, Taylor & Zafman

(57) ABSTRACT

A method and apparatus for purifying acetonitrile from low grade acetonitriles. Low grade acetonitrile from DNA synthesis, HPLC and pharmaceutical drug manufacturing process wastes which comprise acetonitrile, a first set of impurities having a lower boiling temperature than acetonitrile and a second set of impurities having a boiling temperature greater than acetonitrile are processed to produce a purified acetonitrile by first introducing the low grade acetonitrile into a first distillation column and separating the acetonitrile and first set of impurities from the second set of impurities, the acetonitrile and first set of impurities being drawn as a vapor from the first distillation column, the second set of impurities being produced as the first distillation column bottoms. The vapor is then condensed to produce a feed stream that is introduced into a second distillation column where the first set of impurities are separated from the acetonitrile, the purified acetonitrile being collected as the second distillation column bottoms.

37 Claims, 5 Drawing Sheets

METHOD AND APPARATUS FOR PURIFYING LOW GRADE ACETONITRILE AND OTHER CONSTITUENTS FROM HAZARDOUS WASTE

The present patent application is a continuation of prior application Ser. No. 09/419,710, U.S. Pat. No. 6,395,147, filed on Oct. 14, 1999.

FIELD OF THE INVENTION

The present invention relates to the purification of low grade acetonitrile to produce higher grades of acetonitrile.

BACKGROUND OF THE INVENTION

There are currently five types of acetonitrile commonly used in the marketplace: raw acetonitrile, industrial grade acetonitrile, High Performance Liquid Chromatography (HPLC) grade acetonitrile, DNA synthesis grade acetonitrile, and ultra-pure acetonitrile. There are three sources of low grade acetonitrile not yet being utilized.

Raw acetonitrile typically contains up to 50 weight percent acetonitrile and up to 50 weight percent water and is derived from a side reaction during the acrylonitrile manufacturing process. This raw acetonitrile is then purified to meet industry quality specifications for use. Raw acetonitrile is the only source today for making the higher grades of acetonitrile.

Industrial grade acetonitrile is at least 99.75 percent by weight acetonitrile, contains approximately 500 ppm of water and is typically used in gas chromatography applications and agricultural pesticide manufacturing processes.

HPLC grade acetonitrile is a high purity acetonitrile containing at least 99.9 weight percent acetonitrile, a U.V. absorption spectrum measurement of less than 1 angstrom at a 190 nanometer wavelength, and can contain more than 100 ppm of water. HPLC grade acetonitrile is typically used to purify and measure synthetic molecules and DNA probes.

DNA synthesis grade acetonitrile has a purity of at least 99.9 percent by weight acetonitrile, contains approximately 50 ppm or less of water, and has an ultraviolet absorption spectrum measurement of less than 1 angstrom at a 190 nanometer wavelength and zero angstroms at a 260 nanometer wavelength. DNA synthesis grade acetonitrile is typically used as a washing agent, reaction solvent, and a diluent in the DNA synthesis process. DNA synthesis grade acetonitrile is also used in the manufacture of DNA synthesis chemicals.

Ultra-pure acetonitrile has a purity of at least 99.99 weight percent acetonitrile, contains approximately 20 ppm or less of water, and has an ultraviolet absorption spectrum measurement of less than 1 angstrom at a 190 nanometer wavelength. Ultra-high purity acetonitrile is typically used in pharmaceutical drug manufacturing processes.

Low grade acetonitrile is primarily derived from DNA synthesis process waste, HPLC process waste, and pharmaceutical drug manufacturing process waste. These wastes are currently being disposed of by fuel blending (reclamation) or incineration. Low grade acetonitrile is primarily from 30 to 85 percent by weight acetonitrile and contains less than approximately 40 percent water.

DNA synthesis processes typically generate three types of hazardous waste: non-halogenated acetonitrile waste, halogenated dichloromethane waste and aqueous waste. The non-halogenated acetonitrile waste generally consists of a number of constituents which include, but are not limited to: acetonitrile (ACN), dichloromethane (DCM), tetrahydrofuran (THF), pyridine, n-butanol, acetic acid, isobutyl acetate, acetic anhydride, water and other trace constituents including salts and other high molecular fragments.

A number of methods have been developed to purify acetonitrile and various other solvents from raw, industrial grade or higher grade feedstocks. However, there has not been developed an efficient process for purifying acetonitrile from low grade acetonitrile feedstocks.

Prior methods of purifying acetonitrile from raw acetonitrile feedstocks rely on azeotropic or extractive distillation. The method employed is typically dependent on the type and amounts of impurity constituents, including water, the ultimate product purity required, and method economics. Extractive and azeotropic techniques require a separating agent to entrain or extract acetonitrile from its impurities during equilibrium contacting to also obviate having to deal with azeotropes. Acetonitrile is then separated from this added component. For example, U.S. Pat. No. 2,807,573 discloses the purification of acrylonitrile from impure mixtures containing acetonitrile using extractive distillation with water as the separating agent. These processes require relatively large and expensive equipment and have relatively high energy requirements. They also incur additional environmental impact with the handling, loss and disposal of at least one or more additional solvents.

Prior methods of purifying acetonitrile from industrial or higher grade acetonitrile feedstocks include treatment by various absorbents to remove organic impurities (e.g., active alumina, active bauxite, active carbon, special aluminosilicates, molecular sieves, treated clays, Fuller's earth, diatomaceous earth) and to remove water (e.g., active alumina, calcium chloride desiccants, silica gel, aluminosilicates, molecular sieves and other inorganics, including their oxides and carbonates). For example, U.S. Pat. No. 2,107,904 discloses absorbents for absorbing nitriles from liquid hydrocarbon mixtures using alumina and other absorbents. U.S. Pat. No. 2,560,931 discloses the dehydration of acetonitrile by treatment with activated alumina.

Other methods of purifying acetonitrile from industrial or higher grades of acetonitrile have included the use of oxidizing agents such as air, oxygen or ozone, catalytically or not, followed by distillation and/or absorption to remove the oxidized impurities. U.S. Pat. No. 5,426,208 discloses a method of using ozone to oxidize the deleterious impurities of acetonitrile to produce a purified acetonitrile. One problem with this method is that it requires a feedstock that is essentially 99.95 percent acetonitrile.

Fractional crystallization can also be used to purify acetonitrile. However, the use of a fractional crystallization process requires an initial feedstock composition of 99.9+ percent acetonitrile. The fractional crystallization process is also complicated and expensive in terms of initial investment, energy requirements and maintenance.

SUMMARY OF THE INVENTION

A method and apparatus for purifying acetonitrile and other constituents within low grade acetonitrile feedstock is disclosed. In accordance with one embodiment of the invention a process for purifying an acetonitrile feedstock involves purifying a low grade acetonitrile feedstock comprising acetonitrile, a first set of impurities having a lower boiling temperature than acetonitrile and a second set of impurities having a boiling temperature greater than acetonitrile, the process comprising the steps of: a) introducing the feedstock into a first distillation column and separating the acetonitrile and first set of impurities from the second set of impurities, the acetonitrile and first set of impurities being drawn as a vapor from said first distillation column, the second set of impurities being produced as the first distillation column bottoms; b) condensing the vapor to produce a first distillate; and c) introducing the first distillate into a second distillation column and separating the first set of impurities from the acetonitrile, the acetonitrile being produced as the second distillation column bottoms.

In another embodiment, the acetonitrile feedstock includes dichloromethane and tetrahydrofuran. The acetonitrile is purified in the manner described above. The dichloromethane is also purified by directing the vapor from the first distillation column through a first heat exchanger where the temperature is lowered below the dew point of the acetonitrile and tetrahydrofuran. The acetonitrile and tetrahydrofuran are substantially condensed while the dichloromethane vapor is directed to a second heat exchanger where it is condensed.

In yet another embodiment, a DNA synthesizer is provided having its waste effluent directly coupled to an acetonitrile purifier. In one embodiment, the DNA synthesis waste is segregated into acetonitrile waste, dichloromethane waste and detrilylation waste. The acetonitrile waste is coupled to the purifier which includes a first and second distillation column as described above.

In another embodiment, a high performance liquid chromatography instrument is provided having its waste effluent directly coupled to an acetonitrile purifier. The purifier includes a first and second distillation column as described above.

The process of the present invention removes impurities from inexpensive low grade acetonitrile feedstocks to produce industrial, HPLC, DNA synthesis and ultra-pure grades of acetronitrile.

Other features and advantages of the invention will be apparent from the accompanying drawings and and from the detailed description that follows below.

BRIEF DESCRIPTION OF THE DRAWINGS

The present invention is illustrated by way of example in the figures of the accompanying drawings in which like references indicate similar elements and in which.

DETAILED DESCRIPTION

A method and apparatus for purifying acetonitrile and other constituents from low grade acetonitrile is disclosed. In the following description numerous specific details are set forth in order to provide a thorough understanding of the present invention. It will be obvious, however, to one skilled in the art that these specific details need not be employed to practice the invention. In other instances, well known processes, apparatus, materials, etc., have not been described in detail in order to avoid unnecessarily obscuring the present invention.

Figure 1:
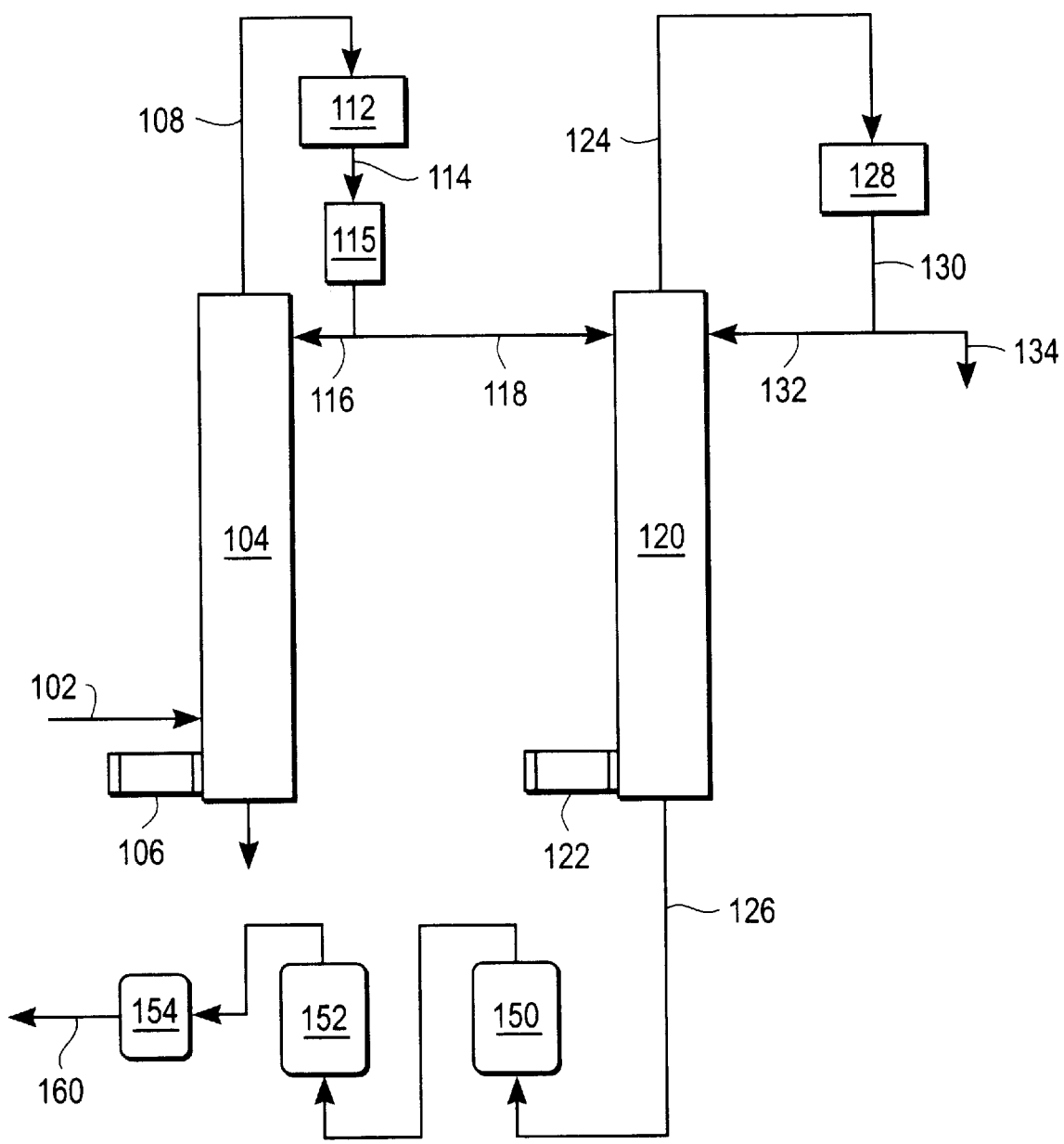
FIG. 1 is a block flow diagram of an acetonitrile purification system in accordance with one embodiment of the invention.

FIG. 1 illustrates an acetonitrile purification/recycling system 100 in one embodiment of the present invention. In accordance with the present invention, a acetonitrile feedstock 102 is directed into the lower portion of a first distillation column 104. By way of example, feedstock 102 is low grade acetonitrile from DNA synthesis waste. The low grade acetonitrile may be provided from other sources such as, but not limited to, HPLC waste and pharmaceutical drug manufacturing waste. As previously discussed, DNA synthesis waste typically contains many constituents which can vary from one process to another. For purposes of describing the purification process of the present invention an acetonitrile feedstock containing acetonitrile, water, tetrahydrofuran, dichloromethane, pyridine, salts and other high molecular weight fragments will be considered. It is appreciated that the acetonitrile feedstock may contain more or fewer constituents. In any event, the acetonitrile feedstock must have a water content of less than what is demanded by the acetonitrile/water azeotrope which is approximately 16 percent by weight water. Preferably, feedstock 102 comprises between zero and 5 percent by weight water, and more preferably between zero and 2 percent by weight water.

Generally, distillation column 104 contains internals such as packing, trays, sieves, bubble caps or similar mechanical configurations which can provide stages of multiple, step wise contact for vapor-liquid streams flowing through the system to approach equilibrium. The number of stages and type of internals used in distillation column 104 will vary depending feedstock composition, feedstock inlet location, reflux ratios, desired column efficiency, etc. As such, the column profile will vary from one application to another. A heat exchanger reboiler 106, located at the bottom of column 104, provides heat to the column.

Figure 2:
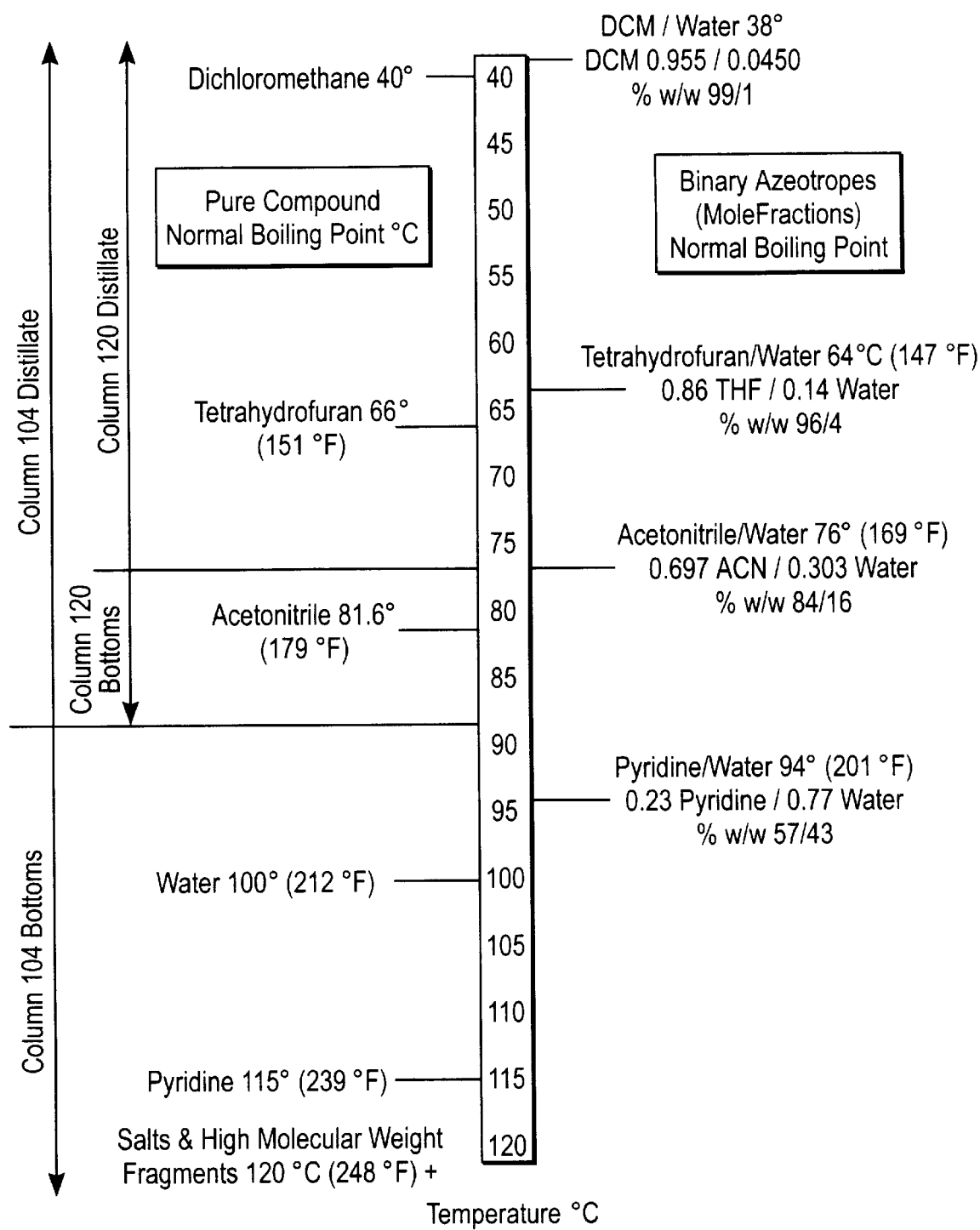
FIG. 2 shows the normal boiling points of feedstock solvents and their respective azeotropes in an example of the invention.

Column 104 is used as a stripping column to affect separation as illustrated and hereinafter described with reference to FIG. 2. FIG. 2 shows the bottoms and distillate composition boiling points of the acetonitrile feedstock when passing through column 104. The normal boiling temperatures of the various components and component azeotropes of feedstock 102 are depicted on the temperature scale of FIG. 2. Based on the known binary azeotropic and normal pure component boiling temperatures, essentially all of the acetonitrile, acetonitrile/water azeotrope, tetrahydrofuran, tetrahydrofuran/water azeotrope, dichloromethane, dichloromethane/water azeotrope are rectified to produce column 104 outlet vapor 108. Upon exiting column 104, vapor 108 is condensed within condenser 112 to produce distillate 114. Reflux 116 is returned to column 104.

The pyridine/water azeotrope, pyridine, water and higher molecular weight liquids are stripped within column 104 and are discarded from the bottoms in stream 110. The objective of the stripping in column 104 is to affect a clean separation of liquids utilizing the difference in boiling points between acetonitrile and the pyridine/water azeotrope. Since the number of stripping and rectification stages required to accomplish this separation is dependent upon feed composition, the location of the feedstock 102 inlet to column 104 will change as a function of feedstock composition. In one embodiment, feedstock inlet 102 is directed sufficiently low in column 104 such that a substantial majority of the stages located within column 104 are used for rectification of the feedstock while substantially fewer stages are used for stripping the feedstock. Ternary and quaternary azeotropes have not been shown to interfere with the separation as projected by the binary azeotropes although ternary and possibly quaternary interactions are likely to exist. The yield of acetonitrile (i.e. process efficiency) is dependent upon the balance of reflux ratio, number of stages within column 104, and the desired distillate 114 profile.

Distillate 114 flows to a receiver 115 that provides temporary liquid accumulation and storage for column 104 reflux and feed 118 to column 120. A heat exchanger reboiler 122, located at the bottom of column 120, provides heat to the column. The internal configuration of column 120 is similar to that of column 104. Feed 118 is introduced into column 120 such that a majority of the stages within the column are used for stripping. As shown in FIG. 2, the acetonitrile/water azeotrope, tetrahydrofuran, tetrahydrofuran/water azeotrope, dichloromethane, and dichloromethane/water azeotrope are rectified to produce distillate 124 while the acetonitrile is stripped to produce bottoms 126. The location of the feed inlet 118 will vary depending on the column profile, feed composition, column operating parameters, etc. Vapor 124 from column 120 is condensed in condenser 128 to form condensate 130. A portion of condensate 130 is directed back as reflux 132 while the remaining portion comprises distillate product 134.

By treating the low grade acetonitrile waste in accordance with the fractional distillation methods herein described, a bottoms 126 comprising 99.9+ percent by weight acetonitrile, less than 500 ppm water and a minimum U.V. absorption of 3.8 angstroms at 190 nanometer wavelength is achieved to produce an industrial grade acetonitrile. Upon exiting column 120, bottoms 126 may be directed through a dehydrator 150, trace impurity absorption apparatus 152, and a filter 154 where the water content, U.V. absorption and insoluble particulates are reduced to produce HPLC, DNA synthesis or ultra-pure grades of acetonitrile. Dehydrator 150 may comprise any of a variety of water removal apparatus including a molecular sieve, desiccant, or other water removal materials known in the art. The trace impurity absorption apparatus 152 may include activated carbon, alumina, silica gel, clay or other trace impurity absorption apparatus known in the art. Filter 154 removes particulates from the purified acetonitrile stream. Filter 154 typically comprises a 0.1–0.5 micron membrane filter, and more preferably, a 0.2 micron membrane filter. In one embodiment, bottoms 126 is further processed to produce a HPLC grade acetonitrile stream 160 comprising 99.9+ percent by weight acetonitrile, less than 200 ppm of water, and an U.V. absorption of less than 1 angstrom at a 190 nanometer wavelength. In another embodiment, bottoms 126 is processed to produce a DNA synthesis grade acetonitrile stream 160 comprising of 99.9+ percent by weight acetonitrile, less than 50 ppm of water, and a U.V. absorption of less than 1 angstrom at a 190 nanometer wavelength. In additional embodiment, bottoms 126 is processed to produce an ultra-pure acetonitrile stream 160 comprising 99.99+ percent by weight acetonitrile, less than 20 ppm of water, and an U.V. absorption of less than 1 angstrom at a 190 nanometer wavelength. The present invention also has the flexibility to attain specific acetonitrile specifications (e.g., water content of less than 4 ppm and a U.V. absorption of less than 0.3 angstroms at 190 nanometer wavelength) by modifying the design and/or operation of the apparatus without unnecessarily exceeding that which is required, thereby optimizing product yield. Table 1 below sets forth the composition and industrial scale rates for the feed, distillate and bottoms streams in accordance with a distillation process of the present invention. Table 2 sets forth the distillation column configurations and reflux ratios. The example of Tables 1 and 2 results in an acetonitrile yield of approximately 85 percent by weight.

TABLE 1

| Stream No. | 102 Lb mol/hr | 110 Lb mol/hr | 118 Lb mol/hr | 130 Lb mol/hr | 126 Lb mol/hr | 160 |
|---|---|---|---|---|---|---|
| Dichloromethane | .017 | <0.001 | .017 | .017 | <0.001 | |
| Tetrahydrofuran | 1.232 | <0.001 | 1.231 | 1.230 | <0.001 | |
| Acetonitrile | 24.253 | 1.443 | 22.810 | 2.211 | 20.599 | 99.99+% |
| Pyridine | 0.182 | 0.182 | <0.001 | <0.001 | <0.001 | |
| N-Butanol | 0.016 | 0.016 | <0.001 | <0.001 | <0.001 | |
| Acetic Acid | 0.020 | 0.020 | <0.001 | <0.001 | <0.001 | |
| Isobutyl Acetate | 0.010 | 0.010 | <0.001 | <0.001 | <0.001 | |
| Acetic Anhydride | 0.015 | 0.015 | <0.001 | <0.001 | <0.001 | |
| Water | 0.666 | 0.009 | 0.657 | 0.657 | <0.001 | <20 ppm |
| Heavy Ends | 0.644 | 0.644 | <0.001 | <0.001 | <0.001 | |
| Total Lb mol/hr | 27.055 | 2.339 | 24.715 | 4.115 | 20.600 | 20.600 |
| Total Lb/hr | 1200 | 162 | 1038 | 193 | 846 | 846 |

TABLE 2

| Distillation Column | 104 | 120 |
|---|---|---|
| Equilibrium Stages | 30 | 25 |
| Feed Stage (From Top) | 28 | 3 |
| Reflux Ratio | 1.8 | 4 |

Product yield is generally a function of feedstock composition and the character of impurities. For example, the higher the concentration of acetonitrile in the feedstock, the greater the yield as set forth in Table 3.

TABLE 3

| ACN Feedstock Concentration (Wt %) | Yield (%) |
|---|---|
| 67.6 | 80.0 |
| 70.5 | 83.9 |
| 76.6 | 84.5 |
| 83.0 | 84.9 |

EXAMPLE

Table 4 sets forth pilot plant results for an actual distillation, dehydration and trace impurity absorption of a low grade acetonitrile feedstock comprising DNA synthesis waste. The feedstock comprised approximately 77.8 percent by weight acetonitrile and approximately 0.17 percent by weight water. Table 5 sets forth the distillation column configurations and reflux ratios, which are a measure of energy efficiency. Both distillation columns were maintained at atmospheric pressure and had feed preheaters to expedite column equilibrium. As seen after distillation, product 126 quality was 99.99+ weight percent pure acetonitrile. The ultraviolet absorption spectrum measurement varied between 3.8 to 4.2 angstroms at a 190 nanometer wavelength. Water content averaged 350 ppm. Product yield was approximately 80 percent.

Product acetonitrile was then passed through two packed columns. The water absorption column was filled with W. R. Grace molecular sieve type A Grade 564-C. The color removal column was packed with Carbon Link BKK 12×40 mesh granular carbon. Residence time for product undergoing treatment in each bed was varied from 1.5 to 25 minutes at 3 to 12 p.s.i.g. The process resulted in a treated product having less than 20 ppm water and a U.V. absorption of 0.45 to 0.65 at a 190 nanometer wavelength (an ultra-pure grade acetonitrile. Although U.V. absorption could be reduced further by reducing bed residence time of the product undergoing treatment, the target specification of less than 1.0 had been attained at virtually 100 percent yields.

TABLE 4

| Stream No. | 102 grams mol/hr | 110 grams mol/hr | 118 grams mol/hr | 130 grams mol/hr | 126 grams mol/hr | 160 |
|---|---|---|---|---|---|---|
| Dichloromethane | 0.079 | 0.012 | 0.067 | 0.067 | 0.000 | |
| Tetrahydrofuran | 0.872 | 0.000 | 0.872 | 0.872 | 0.000 | |
| Acetonitrile | 6.626 | 0.667 | 5.959 | 1.192 | 4.767 | 99.99+% |
| Pyridine | 0.092 | 0.092 | <0.001 | 0.000 | <0.001 | |
| N-Butanol | <0.001 | <0.001 | 0.000 | 0.000 | 0.000 | |
| Acetic Acid | <0.001 | <0.001 | 0.000 | 0.000 | 0.000 | |
| Isobutyl Acetate | <0.001 | <0.001 | 0.000 | 0.000 | 0.000 | |
| Acetic Anhydride | <0.001 | <0.001 | 0.000 | 0.000 | 0.000 | |
| Water | 0.033 | 0.008 | 0.025 | 0.011 | 0.014 | 12–14 ppm |
| Heavy Ends | <0.001 | <0.001 | 0.000 | 0.000 | 0.000 | |
| Total Grams mol/hr | 7.702 | 0.779 | 6.923 | 2.142 | 4.781 | 4.781 |
| Total Grams/hr | 350 | 35 | 315 | 119 | 196 | 196 |

TABLE 5

| Distillation Column | 104 | 120 |
|---|---|---|
| Equilibrium Stages | 30 | 25 |
| Feed Stage (From Top) | 28 | 3 |
| Reflux Ratio | 2.0 | 3.5 |

Figure 3:
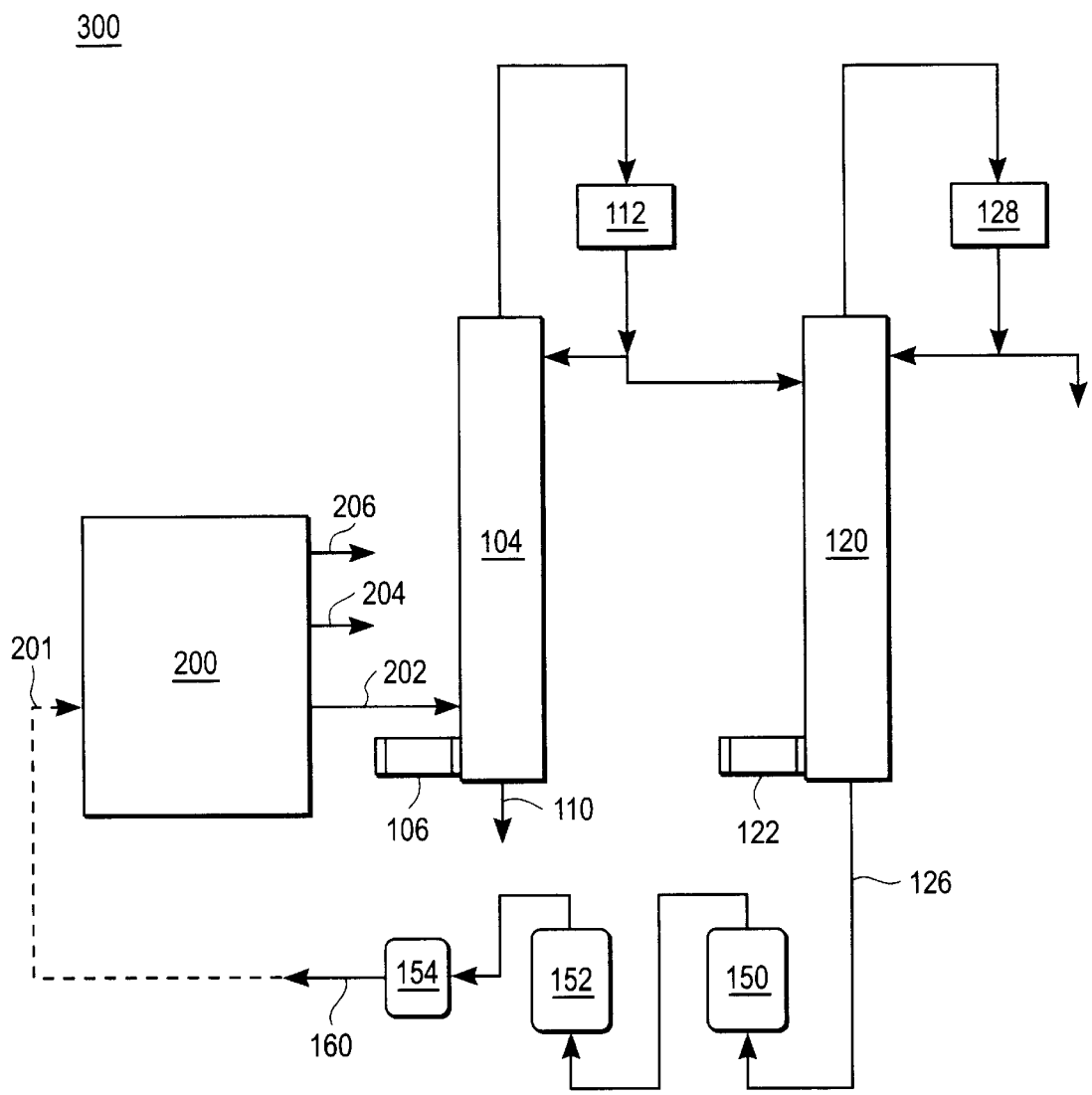
FIG. 3 is a block flow diagram of a recycling system comprising a DNA synthesizer and an acetonitrile purification system.

FIG. 3 shows the purification system 100 of FIG. 1 integrated with a DNA synthesizer 200 to produce a closed-loop acetonitrile recycling system 300. In the embodiment of FIG. 3, DNA synthesizer 200 has three effluent waste streams: (1) non-halogenated acetonitrile waste 202, (2) halogenated dichloromethane waste 204 and (3) detritylation waste 206. The non-halogenated acetonitrile waste stream 202 is fed directly into the inlet of distillation column 104 and is purified according to the processes described above. The purified acetonitrile stream 160 is than directed back into the acetonitrile influent 201 of DNA synthesizer 200. The purified acetonitrile stream is preferably a DNA synthesis grade acetonitrile.

In another embodiment, acetonitrile waste from a high performance liquid chromatography instrument is fed directly into the inlet of distillation column 104 and is purified according to the processes described above. The purified acetonitrile stream 160 is than directed back into the acetonitrile influent of the high performance liquid chromatography instrument. The purified acetonitrile stream is preferably HPLC grade acetonitrile.

In yet another embodiment, acetonitrile waste from a pharmaceutical drug manufacturing process apparatus is fed directly into the inlet of distillation column 104 and is purified according to the processes described above. The purified acetonitrile stream 160 is than directed back into an acetonitrile influent of the pharmaceutical drug manufacturing process. The purified acetonitrile stream is preferably ultra-pure grade acetonitrile.

Figure 4:
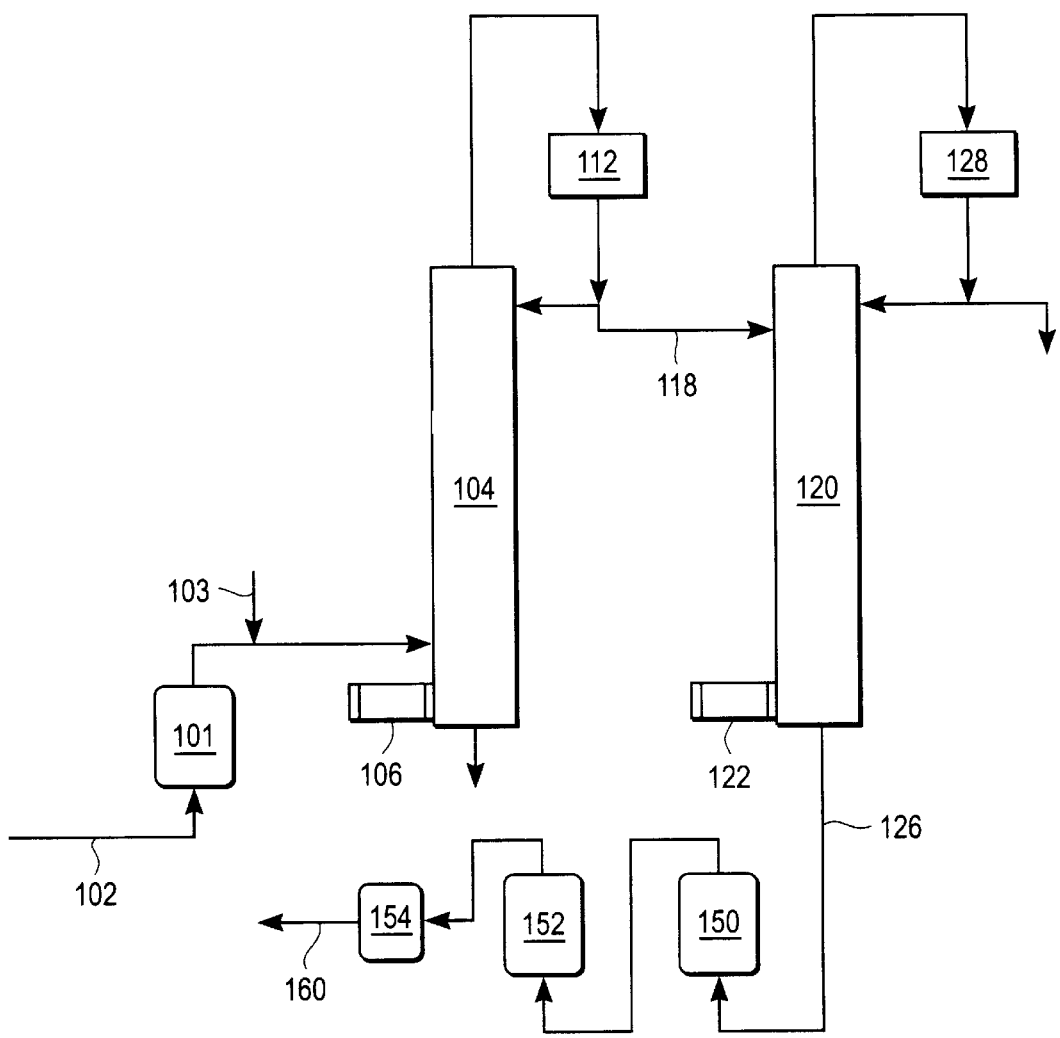
FIG. 4 is a block flow diagram of an acetonitrile purification system in another embodiment of the invention.

With reference:to FIG. 4, an acetonitrile purification system 400 in accordance with another embodiment of the invention is shown. In some instances, it may be beneficial to dehydrate the feedstock prior to the distillation process. As shown in FIG. 4, a dehydrator 101 is provided at the inlet to distillation column 104. Alternatively, or in combination with dehydrator 101, a dehydrator may be provided at the feed inlet to distillation column 120. In this manner, the water content of the distillation feed streams may be controlled to optimize the distillation processes. Raw acetonitrile may be purified in accordance with the methods of the present invention by the use of dehydrator 101. Dehydrator 101 acts to reduce the water content of the raw acetonitrile to produce a feedstock comprising approximately 30 to 85 percent by weight acetonitrile and zero to approximately 16 percent by weight water. Preferably, the water content is reduced to produce a feedstock comprising zero to 5 percent by weight water.

With continuing reference to FIG. 4, an acid 103 may be injected into feedstock inlet 102 to acidify the feedstock. By acidifying the feedstock, alkaline constituents, such as pyridine, are ionized making them incapable of being carried over as distillate in distillation column 104.

Figure 5:
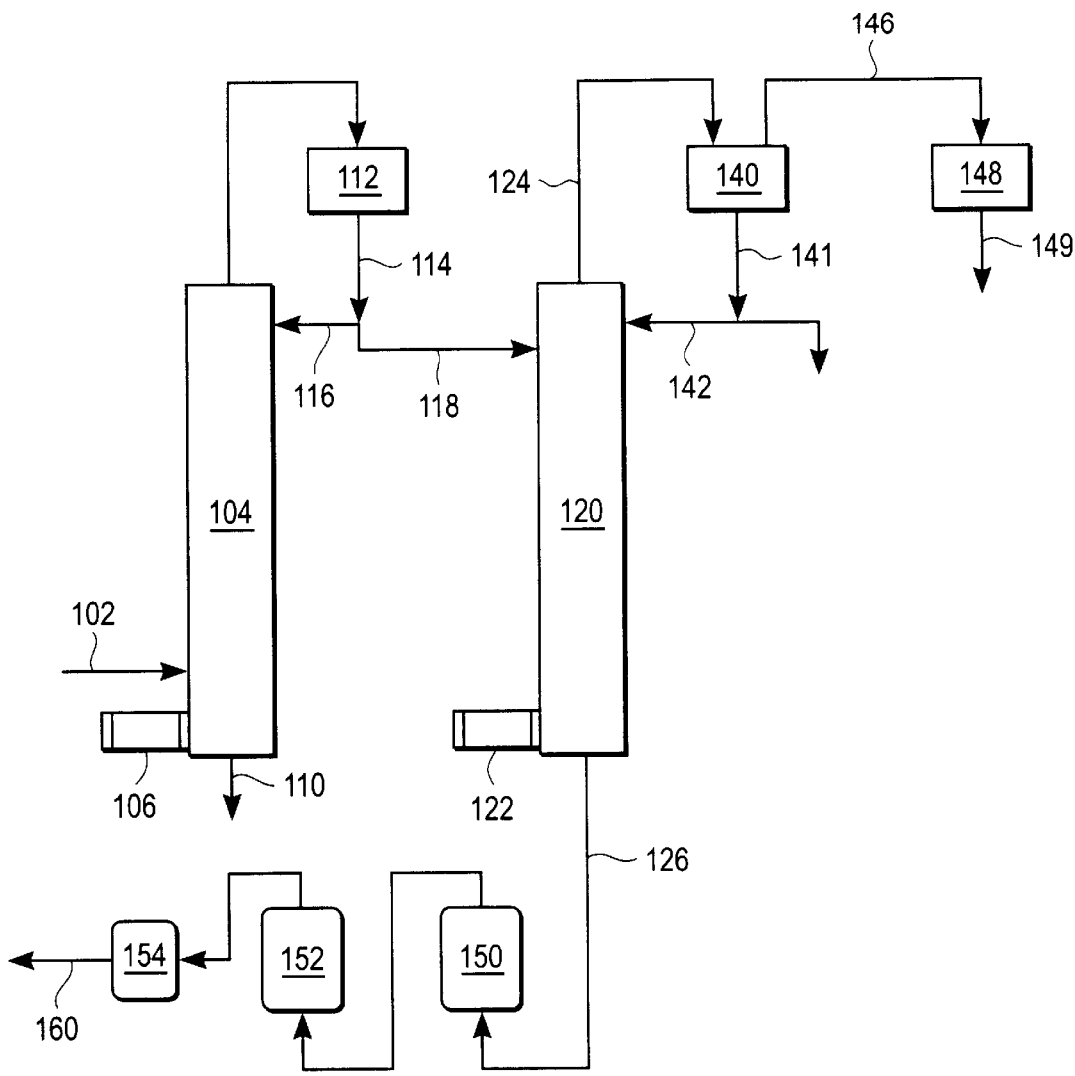
FIG. 5 is a block flow diagram of an acetonitrile and dichloromethane purification system in yet another embodiment of the present invention.

FIG. 5 is a block flow diagram of an acetonitrile purification system 500 in another embodiment of the invention. In the embodiment of FIG. 5, distillate 124 from distillation column 120 is directed through a partial condenser 140 where the vapor temperature is lowered below the dew point of acetonitrile and tetrahydrofuran yet maintained above the dew point of dichloromethane. A portion 142 of the acetonitrile/tetrahydrofuran condensate 141 is directed back as reflux to column 120 while the remaining portion 144 is directed to waste or is further processed. The dichloromethane vapor 146 from condenser 140 is directed to a second condenser 148 where it is condensed. The condensate effluent 149 of condenser 148 is substantially purified dichloromethane which can be recycled through a DNA synthesizer or other dichloromethane source.

In the foregoing specification, the invention has been described with reference to specific exemplary embodiments thereof. It will, however, be evident that various modifications and changes may be made to the specific exemplary embodiments without departing from the broader spirit and scope of the invention as set forth in the appended claims. Accordingly, the specification and drawings are to be regarded in an illustrative rather than a restrictive sense.

What is claimed is:

1. A process comprising:
   a) receiving low grade acetonitrile feedstock selected from the group consisting of DNA synthesis waste, high performance liquid chromatography waste, and pharmaceutical drug manufacturing waste; and
   b) purifying the low grade acetonitrile feedstock in at least a first and a second distillation column to produce a higher grade acetonitrile chosen from the group consisting of: industrial grade acetonitrile, HPLC grade acetonitrile, DNA synthesis grade acetonitrile and ultra-pure grade acetonitrile.

2. The process of claim 1 wherein the low grade acetonitrile feedstock comprises acetonitrile, a first set of impurities having a lower boiling temperature than acetonitrile, and a second set of impurities having a higher boiling temperature than acetonitrile, the process of purifying the low grade of acetonitrile comprising:
   a) introducing the low grade acetonitrile feedstock into said first distillation column and separating the acetonitrile and first set of impurities from the second set of impurities, the acetonitrile and first set of impurities being drawn as a vapor from said first distillation column, the second set of impurities being produced as the first distillation column bottoms;
   b) condensing the vapor to produce a first distillate; and
   c) introducing the first distillate into said second distillation column and separating the first set of impurities from the acetonitrile, the acetonitrile being produced as the second distillation column bottoms.

3. The process of claim 2 wherein an acetonitrile of a higher grade than the low grade acetonitrile feedstock is recovered as distillation bottoms in the second distillation column.

4. The process of claim 3 wherein the higher grade acetonitrile is at least 99.75 percent by weight acetonitrile.

5. The process of claim 2 wherein the first distillation column comprises a plurality of stages, a substantial majority of the stages being used to rectify the acetonitrile and first set of impurities.

6. The process of claim 2 wherein the second distillation column comprises a plurality of stages, a substantial majority of the stages being used to strip the acetonitrile in step b).

7. The process of claim 2 wherein the low grade acetonitrile feedstock is at least partially dehydrated prior to being directed into the first distillation column.

8. The process of claim 2 wherein the distillate from the first distillation column is at least partially dehydrated prior to being directed into the second distillation column.

9. The process of claim 2 wherein the feedstock comprises less than approximately 16 percent by weight water.

10. The process of claim 2 wherein the feedstock comprises 0 to 5 percent by weight water.

11. The process of claim 2 wherein the feedstock comprises 0 to 2 percent by weight water.

12. A process comprising:
   a) directing a raw acetonitrile stream through a dehydrator to produce a low grade acetonitrile feedstock comprising approximately 30 to 85 percent by weight acetonitrile; and
   b) purifying the low grade acetonitrile feedstock in at least a first and a second distillation column to produce a higher grade acetonitrile chosen from the group consisting of: industrial grade acetonitrile, HPLC grade acetonitrile, DNA synthesis grade acetonitrile or ultra-pure grade acetonitrile.

13. The process of claim 12 wherein the low grade acetonitrile feedstock comprises acetonitrile, a first set of impurities having a lower boiling temperature than acetonitrile, and a second set of impurities having a higher boiling temperature than acetonitrile, the process of purifying the low grade of acetonitrile comprising:
   a) introducing the low grade acetonitrile feedstock into said first distillation column and separating the acetonitrile and first set of impurities from the second set of impurities, the acetonitrile and first set of impurities being drawn as a vapor from said first distillation column, the second set of impurities being produced as the first distillation column bottoms;
   b) condensing the vapor to produce a first distillate; and
   c) introducing the first distillate into said second distillation column and separating the first set of impurities from the acetonitrile, the acetonitrile being produced as the second distillation column bottoms.

14. The process of claim 12 wherein the acetonitrile feedstock comprises less than approximately 16 percent by weight water.

15. The process of claim 12 wherein the acetonitrile feedstock comprises 0 to 5 percent by weight water.

16. The process of claim 12 wherein the acetonitrile feedstock comprises 0 to 2 percent by weight water.

17. A process comprising:
   a) receiving low grade acetonitrile from DNA synthesis waste from a DNA synthesizer; and
   b) purifying the low grade acetonitrile in at least a first and a second distillation column to produce a higher grade acetonitrile chosen from the group consisting of: industrial grade acetonitrile, HPLC grade acetonitrile, DNA synthesis grade acetonitrile or ultra-pure grade acetonitrile.

18. The process of claim 17 wherein the low grade acetonitrile comprises acetonitrile, a first set of impurities having a lower boiling temperature than acetonitrile, and a second set of impurities having a higher boiling temperature than acetonitrile, the process of purifying the low grade of acetonitrile comprising:
   a) introducing the low grade acetonitrile into said first distillation column and separating the acetonitrile and first set of impurities from the second set of impurities, the acetonitrile and first set of impurities being drawn as a vapor from said first distillation column, the second set of impurities being produced as the first distillation column bottoms;
   b) condensing the vapor to produce a first distillate; and
   c) introducing the first distillate into said second distillation column and separating the first set of impurities from the acetonitrile, the acetonitrile being produced as the second distillation column bottoms.

19. The process of claim 17 wherein an acetonitrile of a higher grade than the low grade acetonitrile is recovered as distillation bottoms in the second distillation column.

20. The process of claim 19 wherein the distillation bottoms is at least 99.75 percent by weight acetonitrile.

21. The process of claim 17 wherein the low grade acetonitrile is directed from a waste effluent of the DNA synthesizer into a feed inlet of the first distillation column.

22. The process of claim 18 wherein the first distillation column comprises a plurality of stages, a substantial majority of the stages being used to rectify the acetonitrile and the first set of impurities.

23. The process of claim 18 wherein the second distillation column comprises a plurality of stages, a substantial majority of the stages being used to strip the acetonitrile in step b).

24. The process of claim 19 wherein the distillation bottoms is processed to reduce the water content of the acetonitrile to less than 200 parts per million and to reduce the ultraviolet absorption spectrum measurement to less than 1 angstrom at 190 nanometer wavelength.

25. The process of claim 19 wherein the distillation bottoms is processed to reduce the water content of the acetonitrile to less than 50 parts per million and to reduce the ultraviolet absorption spectrum measurement to less than 1 angstrom at 190 nanometer wavelength and an ultraviolet absorption spectrum measurement of zero at a 260 nanometer wavelength.

26. The process of claim 19 wherein the distillation bottoms is processed to reduce the water content of the acetonitrile to less than 20 parts per million and to reduce the ultraviolet absorption spectrum measurement to less than 1 angstrom at 190 nanometer wavelength.

27. The process of claim 17 wherein the low grade acetonitrile is at least partially dehydrated prior to being directed into the first distillation column.

28. The process of claim 18 wherein the first distillate is at least partially dehydrated prior to being directed into the second distillation column.

29. The process of claim 18 wherein the low grade acetonitrile comprises less than approximately 16 percent by weight water.

30. The process of claim 18 wherein the low grade acetonitrile comprises 0 to 5 percent by weight water.

31. The process of claim 18 wherein the low grade acetonitrile comprises 0 to 2 percent by weight water.

32. The process of claim 17 wherein at least a portion of the higher grade acetonitrile is directed into an influent of a DNA synthesizer, the higher grade acetonitrile being of a purity that is equal to or greater than DNA synthesis grade acetonitrile.

33. The process of claim 18 wherein the vapor comprises tetrahydrofuran, dichloromethane and an acetonitrile, at least a portion of the vapor being directed into a first condenser where the vapor temperature is lowered below the dew point of acetonitrile and tetrahydrofuran to allow at least a portion of the dichloromethane vapor to be directed into a second condenser where the vapor temperature is lowered below the dew point of dichloromethane to produce a dichloromethane condensate.

34. The process of claim 33 further comprising the step of directing at least a portion of the dichloromethane condensate into an influent of a DNA synthesizer.

35. A process for separating dichloromethane from DNA synthesis waste, the DNA synthesis waste comprising tetrahydrofuran, dichloromethane and acetonitrile, the process comprising the steps of:
   a) introducing the DNA synthesis waste into a first distillation column, distilling the DNA synthesis waste to create a vapor comprising tetrahydrofuran, dichloromethane and acetonitrile; and
   b) directing at least a portion of the vapor into a first condenser where the vapor temperature is lowered below the dew point of acetonitrile and tetrahydrofuran.

36. The process of claim 35 further comprising the step of directing at least a portion of the dichloromethane vapor into a second condenser where the vapor temperature is lowered below the dew point of dichloromethane to produce a dichloromethane condensate.

37. The process of claim 36 further comprising directing at least a portion of the dichloromethane condensate into an influent of a DNA synthesizer.

* * * * *